US006991681B2

(12) United States Patent
Yoe

(10) Patent No.: US 6,991,681 B2
(45) Date of Patent: Jan. 31, 2006

(54) METHOD AND APPARATUS FOR COATING AN IMPLANTABLE DEVICE

(75) Inventor: Brandon J. Yoe, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/371,132

(22) Filed: Feb. 19, 2003

(65) Prior Publication Data

US 2003/0150380 A1  Aug. 14, 2003

Related U.S. Application Data

(62) Division of application No. 09/755,463, filed on Jan. 5, 2001, now Pat. No. 6,544,582.

(51) Int. Cl.
*B05C 3/02* (2006.01)
(52) U.S. Cl. .................................... 118/404; 118/109
(58) Field of Classification Search ............... 118/264, 118/125, 56, 109, 427, 506, 405, 420, DIG. 18, 118/DIG. 19, 404, 50, 57, 120, DIG. 13, 118/DIG. 11, DIG. 12
See application file for complete search history.

(56) References Cited

U.S. PATENT DOCUMENTS

| | | | |
|---|---|---|---|
| 19,216 A * | 2/1858 | Thayer et al. | |
| 490,682 A * | 1/1893 | Roemer | |
| 2,404,507 A * | 7/1946 | Link | |
| 3,987,219 A | 10/1976 | Arvidsson | 427/297 |
| 4,278,694 A * | 7/1981 | Chiu et al. | |
| 4,356,218 A * | 10/1982 | Chiu et al. | |
| 4,532,277 A | 7/1985 | Wingler | 524/37 |
| 4,552,781 A | 11/1985 | Cannady, Jr. et al. | 427/57 |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 5,037,377 A | 8/1991 | Alonso | 600/36 |
| 5,071,674 A | 12/1991 | Nogues et al. | 427/57 |
| 5,094,557 A * | 3/1992 | Nelson et al. | |
| 5,340,614 A | 8/1994 | Perman et al. | 427/2.24 |
| 5,447,793 A * | 9/1995 | Montsinger | 428/373 |
| 5,464,650 A | 11/1995 | Berg et al. | 427/2.3 |
| 5,527,337 A | 6/1996 | Stack et al. | 606/198 |
| 5,697,980 A | 12/1997 | Otani et al. | 623/16 |
| 5,700,286 A | 12/1997 | Tartaglia et al. | 623/1 |
| 5,713,949 A | 2/1998 | Jayaraman | 623/1 |
| 5,766,710 A | 6/1998 | Turnlund et al. | 428/36.1 |
| 5,769,883 A | 6/1998 | Buscemi et al. | 623/1 |
| 5,817,328 A | 10/1998 | Gresser et al. | 424/426 |
| 5,843,172 A | 12/1998 | Yan | 623/1 |
| 5,873,904 A | 2/1999 | Ragheb et al. | 623/1 |

(Continued)

FOREIGN PATENT DOCUMENTS

WO  WO 98/23228  6/1998

*Primary Examiner*—Brenda A. Lamb
(74) *Attorney, Agent, or Firm*—Squire, Sanders & Dempsey L.L.P.

(57) ABSTRACT

An apparatus and methods for applying a coating to an implantable device. The implantable device can include depots formed in the outer surface thereof to receive the coating. The coating can include a polymer and a solvent applicable to the surface of the implantable device including the depots. The application of the composition is performed under a pressure, which can reduce the surface tension and/or molecular adhesion force of the composition. The reduced surface tension and/or adhesion force allows gas bubbles within the depots to be removed while the composition is being driven into the depots.

18 Claims, 8 Drawing Sheets

U.S. PATENT DOCUMENTS

| | | | |
|---|---|---|---|
| 5,993,374 A | 11/1999 | Kick | 600/8 |
| 6,149,681 A | 11/2000 | Houser et al. | 623/1.12 |
| 6,253,443 B1 | 7/2001 | Johnson | 29/557 |
| 6,254,632 B1 | 7/2001 | Wu et al. | 623/1.15 |
| 6,273,908 B1 | 8/2001 | Ndondo-Lay | 623/1 |
| 6,306,165 B1 | 10/2001 | Patnaik et al. | 623/1.43 |
| 6,387,179 B1 * | 5/2002 | Anderson et al. | 118/125 |
| 6,419,745 B1 * | 7/2002 | Burkett et al. | |

* cited by examiner

METHOD AND APPARATUS FOR COATING AN IMPLANTABLE DEVICE

CROSS REFERENCE

This is a divisional application of U.S. Ser. No. 09/755,463, which was filed on Jan. 5, 2001 now U.S. Pat. No. 6.544,582.

BACKGROUND OF THE INVENTION

1. Field of the Invention

The present invention relates generally to implantable devices. More particularly, the present invention is directed to a method and apparatus for coating an implantable device having a plurality of depots.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

A problem associated with the above procedure includes formation of intimal flaps or torn arterial linings which can collapse and occlude the vessel after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an implantable device, such as a stent, may be implanted.

Stents are scaffoldings, usually cylindrical or tubular in shape, which function to physically hold open and, if desired, to expand the wall of the vessel. Typically stents are capable of being compressed, so that they may be inserted through small cavities via catheters, and then expanded to a larger diameter once they are at the desired location.

Although stents are significant innovations in the treatment of occluded vessels, there remains a need for administering therapeutic substances to the treatment site. Systemic administration of the therapeutic substance often produces adverse or toxic side effects for the patient. Local delivery of therapeutic substances, by contrast, provides a smaller overall dosage that is concentrated at a specific treatment site. Local delivery can produce fewer side effects and achieve more effective results.

One technique for the local delivery of therapeutic substances employs medicated coatings on implantable devices. A typical method for medicating an implantable device includes applying a composition containing a polymer, a solvent, and a therapeutic substance to the implantable device using conventional techniques, for example, a dip-coating technique.

A recently developed type of stent includes a plurality of pores, called "depots" herein, that are formed in the outer surface of the stent. The depots are sized and shaped to contain the composition to ensure that a measured dosage of the composition is delivered with the stent to the specific treatment site. Unfortunately, when such stents are coated using conventional techniques, undesirable pockets of air can become trapped in the depots. The trapped air reduces the volume available in the depot for holding the composition. The uncertainty regarding the amount of composition loaded in the depots can cause inaccurate dosages being delivered to treatment sites and result in ineffective treatment.

SUMMARY OF THE INVENTION

The present invention provides an apparatus and methods of applying a coating to an implantable device (i.e., a device that is designed to be implanted in a human or animal body). Beneficially, the implantable device has depots formed in the outer surface thereof to receive the coating. The present invention provides an effective and economical way for preparing the implantable devices to carry and thus deliver a substantially full dosage of therapeutic substances to a specific treatment site.

An exemplary method within the present invention includes applying a composition including a polymer and a solvent to the surface of the implantable device including the depots. The application of the composition is performed under pressure, which can reduce the surface tension and/or molecular adhesion force of the composition. The reduced surface tension and/or adhesion force allows air pockets formed within the depots to escape while the composition is being driven into the depots.

In another aspect of the present invention, an apparatus is provided for loading an implantable device, which can have at least one depot formed thereon, with a substance. The apparatus includes a mandrel, which supports the implantable device during the loading operation. The apparatus also includes a funnel, which can be submerged in a bath of the substance. The mandrel with the implantable device mounted thereon can be moved within the funnel, which creates a pressure gradient over the implantable device. The pressure gradient reduces a surface tension of the substance, which allows any gas which may have become trapped in the depot during loading to escape.

These and other embodiments of the present invention will also become readily apparent to those skilled in the art from the following detailed description of the embodiments having reference to the attached figures, the invention not being limited to any particular embodiment(s) disclosed.

DETAILED DESCRIPTION

The development of an implantable device that is capable of delivering a composition containing a therapeutic substance is dependent, among other things, on the ability to load or coat the composition on the implantable device. Depots formed on the implantable device have a particular volume intended to be filled with the composition to increase the amount of the composition that can be delivered from the implantable device to the target treatment site. As previously mentioned, a small body of gas within a liquid (i.e., a bubble) can become trapped in the depot during loading. The trapped bubble can occupy valuable space within the depot that would otherwise be filled with the composition. The surface tension and/or molecular cohesive forces of the composition can be a formidable impediment to the removal of the trapped bubble. As used herein, surface tension refers to the measure of the energy required to reach below the surface of a liquid bulk and bring molecules to the surface to form a new area.

As mentioned above, implantable devices that may be treated according to the methods of the present invention include stents, among other possibilities. An implanted stent having the above-described coating is useful for treating occluded regions of blood vessels caused by thrombosis and/or restenosis, among other possible uses.

Implantable devices may be placed in a wide array of blood vessels, both arteries and veins. Briefly, an angiogram is first performed to determine the appropriate positioning for implantable device therapy. An angiogram is typically accomplished by using a catheter to inject a radiopaque contrasting agent into an artery or vein as an X-ray is taken. A guidewire is then advanced through the lesion or proposed site of treatment. Over the guidewire is passed a delivery catheter, which allows an implantable device to be inserted into the passageway. The delivery catheter is inserted either percutaneously or by surgery into the femoral artery, brachial artery, femoral vein, or brachial vein and advanced into the appropriate blood vessel by steering the catheter through the vascular system under fluoroscopic guidance. The implantable device may then be positioned at the desired area of treatment. A post-insertion angiogram may be used to confirm appropriate positioning.

Figure 1A:
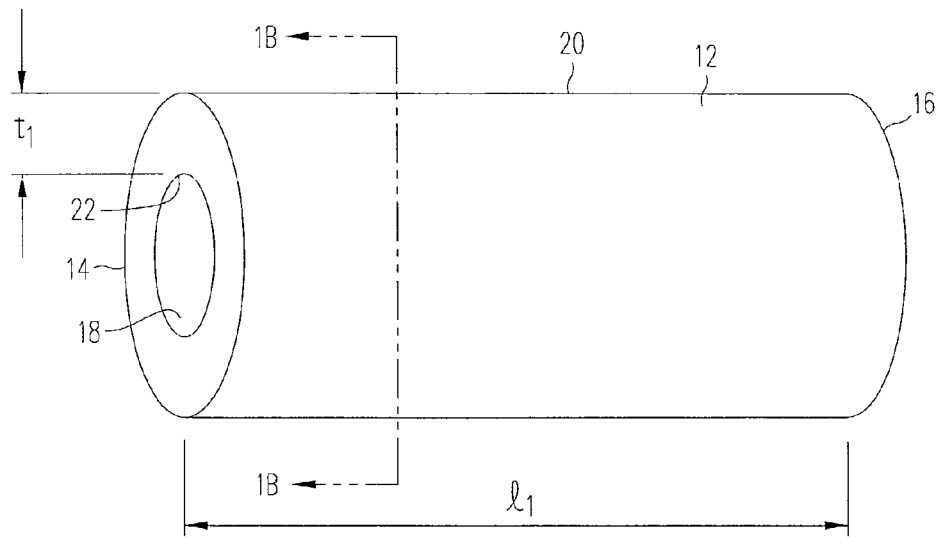
FIG. 1A is a simplified perspective view of an implantable device with a central hollow bore.
Figure 1B:
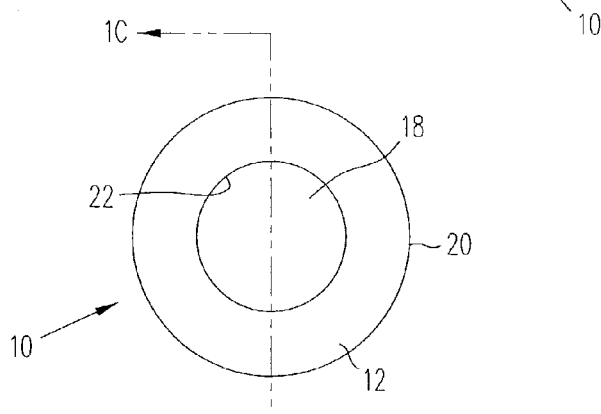
FIG. 1B is a simplified cross-sectional side view of the implantable device of FIG. 1A taken along line 1B—1B of FIG. 1A.
Figure 1C:
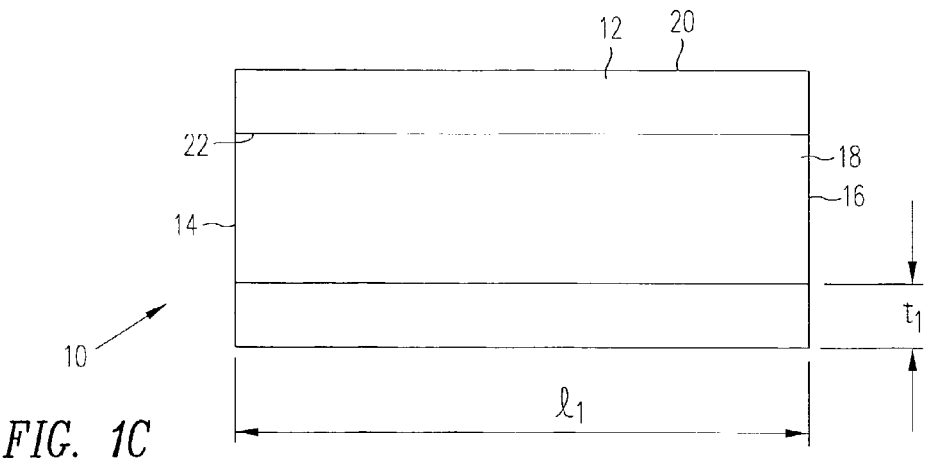
FIG. 1C is a simplified side view of the implantable device of FIG. 1B taken along line 1C—1C of FIG. 1B.

FIGS. 1A, 1B, and 1C provide views of an exemplary implantable device 10, in accordance with the present invention. Implantable device 10 can be any implantable device, examples of which include self-expandable stents, balloon-expandable stents, and the like. In one embodiment, implantable device 10 is a generally tubular structure that includes a body 12 having a first end 14 and an opposing second end 16. A central hollow bore 18 extends longitudinally through body 12 from first end 14 to second end 16 giving body 12 a thickness t, between an outer surface 20 and an inner surface 22. Implantable device 10 can have any suitable length $l_1$. The actual values of length l and thickness $t_1$ depend on the usage and application of implantable device 10.

The surface properties of implantable device 10 may vary according to the desired use of implantable device 10. In some embodiments, inner surface 22 and/or outer surface 20 of implantable device 10 is polished using conventional electropolishing methods, abrasive slurry methods, or other polishing methods known to those of ordinary skill in the art. In other embodiments, portions of outer surface 20 are roughened by the creation of asperities while inner surface 22 remains smooth. Asperities can be created by projecting a stream of pressurized grit onto outer surface 20. Asperities can also be formed by removing material from outer surface 20, for example, by chemical etching with or without a patterned mask. Alternatively, asperities can be formed by adding material to outer surface 20, for example, by welding powder to outer surface 20 or by sputtering onto outer surface 20.

Implantable device 10 can be made of a metallic material or an alloy such as, but not limited to, stainless steel, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The implantable device may also be made from bioabsorbable or biostable polymers. A polymeric implantable device should be chemically compatible with any substance to be loaded onto the implantable device.

Figure 2A:
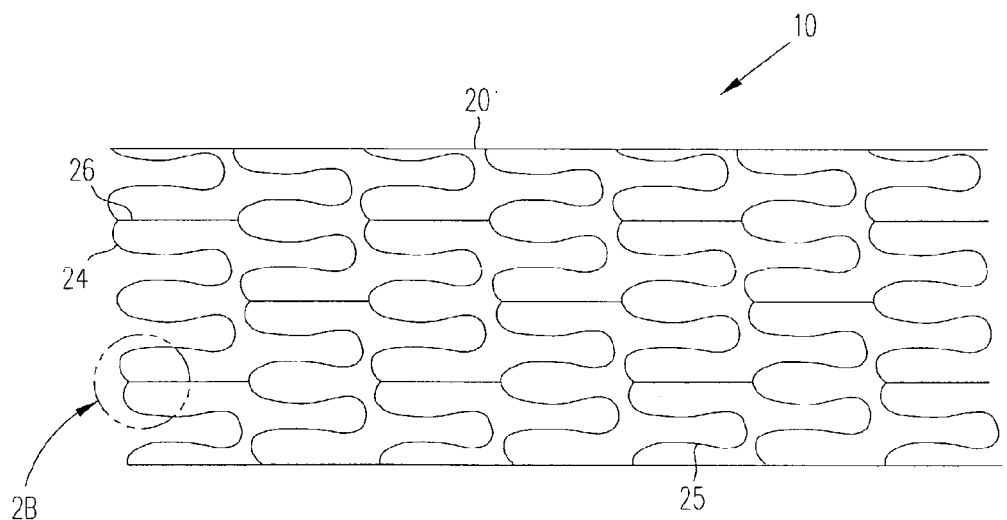
FIG. 2A is a simplified side view of an exemplary stent formed of thread elements engaged to one another by connecting elements.

FIG. 2A is a side view of a stent, which is an exemplary type of implantable device 10. In FIG. 2A, body 12 is formed from a plurality of rings 24 each having arms 25 and a link 26. Arms 25 of neighboring rings 24 are engaged to one another by links 26. It should be understood that the underlying structure of implantable device 10 can be of virtually any design.

Figure 2B:
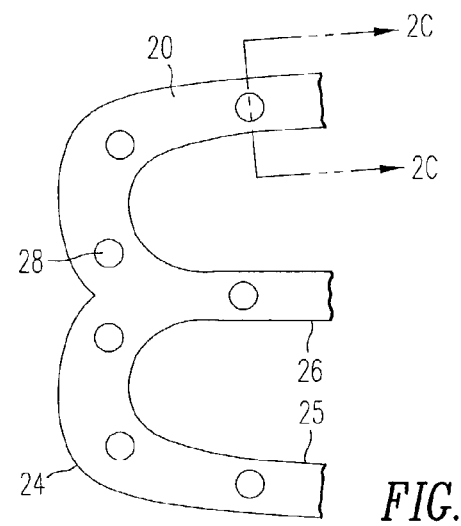
FIG. 2B is an enlarged view of circled section 2B of the stent of FIG. 2A, wherein the thread elements and connecting elements have depots formed therein.

FIG. 2B illustrates the portion of the exemplary implantable device 10 shown in circle 2B of FIG. 2A. FIG. 2B shows that arms 25 and a link 26 of ring 24 each have a plurality of depots 28 formed in outer surface 20. Depots 28, which may also be referred to as pores or cavities, can be formed in virtually any implantable device 10 structure at any preselected location within implantable device 10. The location of depots 28 within implantable device 10 varies according to intended usage and application. Depots 28 may be formed on implantable device 10 by exposing outer surface 20 to an energy discharge from a laser, such as, but not limited to, an excimer laser. Alternative methods of forming such depots 28 include but are not limited to, physical and chemical etching techniques. Such techniques are well-known to one of ordinary skill in the art.

Figure 2C:
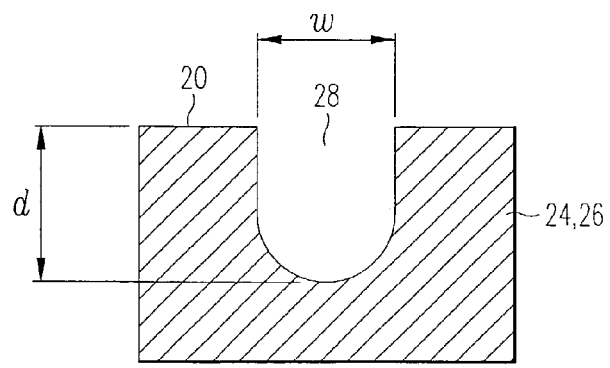
FIG. 2C is a cross-sectional view of a depot within the stent of FIG. 2B taken along line 2C—2C of FIG. 2B.

FIG. 2C is a cross-sectional view of a single depot 28 of FIG. 2B. Depot 28 may have any preselected depth d, width w, and geometrical configuration. Depth d and width w of depot 28 typically depend on the material and dimensions of implantable device 10 and the type and amount of substances deposited within depot 28 as well as on the clinical purpose and usage of implantable device 10. Depth d and width w of the individual depots 28 formed on a single implantable device 10 can vary relative to one another. Depot 28 may be formed in a variety of selected geometrical shapes including, but not limited to, generally cylindrical shapes, generally conical shapes, generally round shapes, elongated trenches, and irregular shapes.

A composition to be applied to implantable device 10 is prepared by conventional methods wherein all components are combined and blended. More particularly, in accordance with one embodiment a predetermined amount of a polymer is added to a predetermined amount of a solvent. The term polymer is intended to include a product of a polymerization reaction inclusive of homopolymers, copolymers, terpolymers, etc., whether natural or synthetic, including random, alternating, block, graft, crosslinked, hydrogels, blends, compositions of blends and variations thereof.

The polymer should be biocompatible, for example a polymeric material which, in the amounts employed, is non-toxic and chemically inert as well as substantially non-immunogenic and non-inflammatory. Suitable polymeric materials include, but are not limited to, bioabsorbable polymers, biomolecules, and biostable polymers. A bioabsorbable polymer breaks down in the body and is not present sufficiently long after delivery to cause an adverse local response. Bioabsorbable polymers are gradually absorbed or eliminated by the body by hydrolysis, metabolic process, bulk, or surface erosion. Examples of bioabsorbable materials include, but are not limited to, polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polyorthoester, polyanhydride, poly(glycolic acid), poly(glycolic acid-cotrimethylene carbonate), polyphosphoester, polyphosphoester urethane, poly (amino acids), cyanoacrylates, poly (trimethylene carbonate), poly(iminocarbonate), copoly (ether-esters), polyalkylene oxalates, polyphosphazenes, polyiminocarbonates, and aliphatic polycarbonates. Biomolecules such as heparin fibrin, fibrinogen, cellulose, starch, and collagen are typically also suitable. A biostable polymer does not break down in the body, and thus a biostable polymer is present in the body for a substantial amount of time after delivery unless some modification is made to allow the polymer to break down. Examples of biostable polymers include, but are not limited to, PARYLENE, PARYLAST, polyurethane (for example, segmented polyurethanes such as BIOSPAN), polyethylene, polyethlyene teraphthalate, ethylene vinyl acetate, silicone and polyethylene oxide.

The solvent can be any single solvent or a combination of solvents capable of dissolving the polymer. The particular solvent or combination of solvents selected is dependent on factors such as the material from which implantable device 10 is made and the particular polymer selected. Representative examples of suitable solvents include, but are not limited to, aliphatic hydrocarbons, aromatic hydrocarbons, alcohols, ketones, dimethyl sulfoxide (DMSO), tetrahydrofuran (THF), dihydrofuran (DHF), dimethylacetamide (DMAC), acetates and combinations thereof.

The addition of the polymer to the solvent may be conducted at ambient pressure and under anhydrous atmosphere. If necessary, gentle heating and stirring and/or mixing can be employed to effect dissolution of the polymer into the solvent, for example about 12 hours in a water bath at about 60° C.

The polymer can constitute from about 0.5% to about 20%, or more particularly from about 5% to about 10%, by weight of the total weight of the composition, and the solvent can constitute from about 80% to about 99.5%, or more particularly from about 90% to about 95%, by weight of the total weight of the composition. A specific weight ratio is dependent on factors such as the material from which implantable device 10 is made, the geometrical structure of implantable device 10 and of depots 28, the particular polymer or combination of polymers selected, the particular solvent or combination of solvents selected, the solubility of the selected polymer(s) in the selected solvent(s), and the method by which the composition will be applied to implantable device 10.

In one embodiment, sufficient amounts of a therapeutic substance or a combination of therapeutic substances are dispersed in the blended composition of the polymer and the solvent. In this embodiment, the polymer can constitute from about 0.5% to about 20% by weight of the total weight of the composition, the solvent can constitute from about 60% to about 99.4% by weight of the total weight of the composition, and the therapeutic substance can constitute from about 0.1% to about 20% by weight of the total weight of the composition. More particularly, the concentration of the therapeutic substance in the composition may be from about 1–9 times the concentration of the polymer in the composition.

In addition to the factors listed above, selection of a specific weight ratio of the polymer and the solvent in embodiments in which a therapeutic substance is employed is dependent on factors such as the type and amount of therapeutic substance employed. The particular weight percentage of a therapeutic substance mixed within the composition depends on factors such as the type of therapeutic substance selected, the solubility of the selected therapeutic substance, the duration of the release, the cumulative amount of release, and the release rate that is desired.

The therapeutic substance may be in true solution or saturated in the composition. If the therapeutic substance is not completely soluble in the composition, operations such as gentle heating, mixing, stirring, and/or agitation can be employed to effect homogeneity of the residues. However, care should be taken to ensure that the use of heat to effect dissolution does not also cause denaturation of a heat-sensitive therapeutic substance such as, but not limited to, a proteinaceous therapeutic substance.

Alternatively, the therapeutic substance may be encapsulated in a sustained delivery vehicle such as, but not limited to, a liposome or an absorbable polymeric particle. The preparation and use of such sustained delivery vehicles are well known to those of ordinary skill in the art. The sustained delivery vehicle containing the therapeutic substance is then suspended in the composition.

Inclusion of the therapeutic substance in the composition should not adversely alter the composition or characteristic of the therapeutic substance. Accordingly, the particular therapeutic substance is selected for mutual compatibility with the other components of the composition.

In some embodiments, the therapeutic substance includes, but is not limited to, antineoplastic, antimitotic, antiinflammatory, antiplatelet, anticoagulant, antifibrin, antithrombin, antiproliferative, antibiotic, antioxidant, antiallergic, antiangiogenic, and angiogenic substances as well as combinations thereof. Examples of such antineoplastics and/or antimitotics include paclitaxel (e.g., TAXOL by Bristol-Myers Squibb Co., Stamford, Conn.), docetaxel (e.g., TAXOTERE from Aventis S.A., Frankfurt, Germany) methotrexate, azathioprine, vincristine, vinblastine, fluorouracil, doxorubicin hydrochloride (e.g., ADRLAMYCIN from Pharmacia & Upjohn, Peapack N.J.), and mitomycin (e.g., MUTAMYCIN from Bristol-Myers Squibb Co., Stamford, Conn.) Examples of such suitable antiinflammatories include glucocorticoids such as dexamethasone, methylprednisolone, hydrocortisone and betamethasone, superpotent glucocorticoids such as clobustasol, halobetasol, and diflucortolone, and nonsteroidal antiinflammatories such as aspirin, indomethacin and ibuprofen. Examples of such antiplatelets, anticoagulants, antifibrin, and antithrombins include sodium heparin, low molecular weight heparins, heparinioids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.) Examples of such cytostatic or antiproliferative agents include actinomycin D as well as derivatives and analogs thereof (manufactured by Sigma-Aldrich, Milwaukee, Wis.; or COSMEGEN available from Merck & Co., Inc., Whitehouse Station, N.J.), angiopeptin, angiotensin converting enzyme inhibitors such as captopril (e.g., CAPOTEN and CAPOZIDE from Bristol-Myers Squibb Co., Stamford, Conn.), cilazapril or lisinopril (e.g., PRINIVIL and PRINZIDE from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Examples of antiangiogenic agents include thalidomide and angiostatin. Examples of angiogenic agents include vascular endothelial cell growth factor (VEGF) and fibroblast growth factor (FGF). Examples of arteriogenic agents include histimine, MCP-1, lipopolysaccharide, and β-FGF. Other therapeutic substances or agents that may be used include alpha-interferon, genetically engineered epithelial cells, and dexamethasone. While the preventative and treatment properties of the foregoing therapeutic substances or agents are well-known to those having ordinary skill in the art, the substances or agents are provided by way of example and are not meant to be limiting. Other therapeutic substances are equally applicable for use with the disclosed methods and compositions.

In other embodiments, the therapeutic substance may be a radioactive isotope. Examples of radioactive isotopes include, but are not limited to, phosphorus (P32), palladium (Pd103), cesium (Cs131), and iodine (I125).

In still other embodiments, the therapeutic substance is a nucleic acid or a protein. Examples of such nucleic acids include phosphorodiamidate morpholino oligomers (PMO), cyclic-3'–5'-adenosine monophosphate (8-C1-cAMP), Antisense oligonucleotides, and various nucleic acids encoding for growth factors, such as vascular endothelial cell growth factor (VEGF) and fibroblast growth factor (FGF). Examples of proteins include growth factors such as VEGF and FGF.

In addition, the composition may include more than one therapeutic substance. In such embodiments, the number, type, and ratio of therapeutic substances within the composition are treatment-specific. However, the substances within the composition should be mutually compatible, such that the characteristics, effectiveness, and physical structure of the substances are not adversely altered. Therapeutic substances that are not mutually compatible should be isolated from one another within the composition by, for example, encapsulating one or both of the therapeutic substances within separate sustained delivery vehicles.

In still other embodiments, the composition may include a radiopaque substance. Such substances help to facilitate implantable device usage in radiotherapeutic procedures. An example of a radiopaque substance is gold.

Figure 3A:
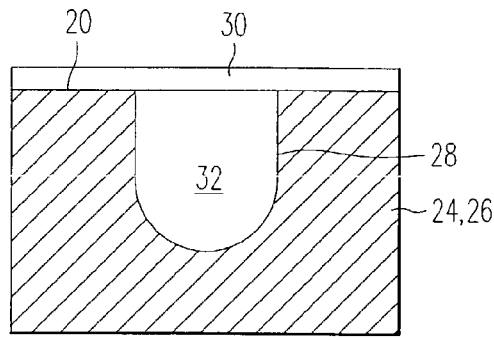
FIGS. 3A, 3B, 3C, and 3D illustrate the stent of FIG. 2C after the composition has been applied.
Figure 3B:
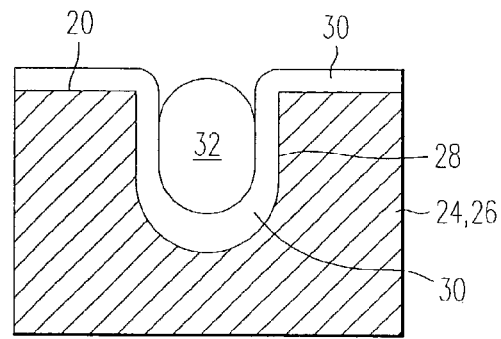
Figure 3C:
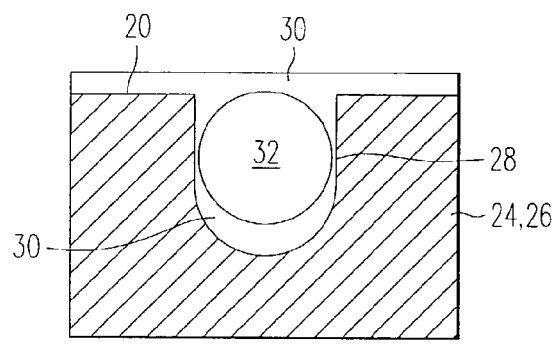
Figure 3D:
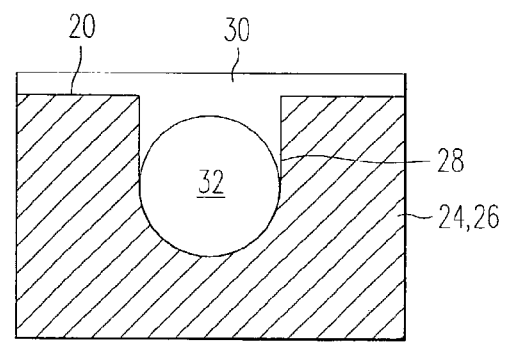

As described further below, the composition is applied to implantable device 10 to form a coating thereon. As shown in FIGS. 3A–3D, undesirable air pockets 32 form in depots 28 when conventional coating methods are used. The air pockets 32 prevent composition 30 from completely filling depots 28. For example, FIG. 3A illustrates an embodiment in which composition 30 is deposited solely on outer surface 20. Depot 28 contains an air pocket 32 rather than composition 30. Alternatively, some amount of composition 30 may enter depot 28, such that depot 28 is from about 0.1% to about 50% filled with composition 30. The portion of depot 28 not filled with composition 30 typically contains an air pocket 32. Air pocket 32 within depot 28 may form above, between, or below areas containing composition 30, as depicted in FIGS. 3B, 3C, and 3D, respectively. The amount of composition 30 that enters depot 28, if any, depends, in part, on the geometry of depot 28 and the surface tension of composition 30.

Figure 4:
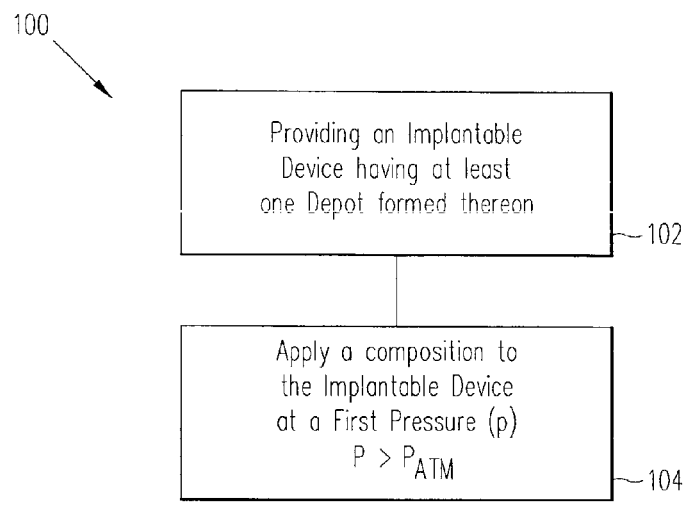
FIG. 4 is a flowchart illustrating exemplary methods of coating an implantable device.

FIG. 4 is flow diagram describing an embodiment of the method of the present invention. In act 102, implantable device 10 is provided, which includes at least one to a plurality of depots 28. Composition 30 is applied to implantable device 10 at a pressure P in act 104.

Figure 5:
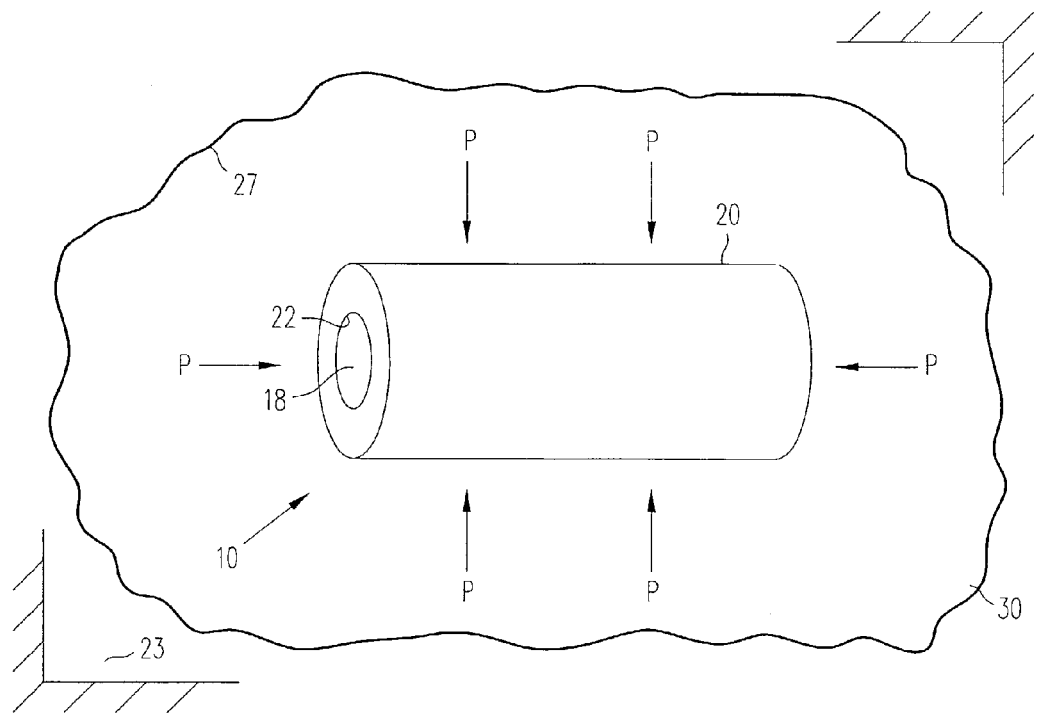
FIG. 5 illustrates the application of an increased pressure to the implantable device of FIG. 1A following application of the composition.

In one embodiment, with reference to FIGS. 4 and 5, implantable device 10 is disposed in an airtight chamber 23 in a bath 27 of composition 30. In act 104, implantable device 10 is subjected to a pressure, such as a hydrostatic pressure P, which can be uniformly applied to implantable device 10 and composition 30. Hydrostatic pressure P at which composition 30 is applied to implantable device 10 is greater than atmospheric pressure ($P_{atm}$). The actual hydrostatic pressure P selected depends, at least in part, on the shape and size of depots 28, the surface finish of implantable device 10, and the viscosity of composition 30.

Compositions 30 having higher viscosity (e.g., 20% polymer by weight), typically require using higher pressures (e.g., 58.8 PSI (405 kPa)), while compositions 30 having lower viscosity (e.g., 0.5% polymer by weight), typically require using lower pressures (e.g., 29.4 PSI (203 kPa)). Regardless of the viscosity of compositions 30, pressure P applied should not be so high as to cause phase separation or precipitation.

The duration for which pressure P is applied depends, in part, on the viscosity of composition 30 and the actual pressure P applied. Compositions 30 having higher viscosity (e.g., 20% polymer by weight), typically require that pressure P be applied for a longer duration (e.g., 10 minutes), while compositions 30 having lower viscosity (e.g., 0.5% polymer by weight), typically require that pressure P be applied for a shorter duration (e.g., 0.5 minute). Similarly, higher pressures (e.g., 58.8 PSI (405 kPa)), typically are applied for a shorter duration (e.g., 5 minutes), while lower pressures (e.g., 29.4 PSI), typically are applied for a longer duration (e.g., 20 minutes).

By way of example and not limitation, hydrostatic pressure P can range from about 29.4 PSI (203 kPa) to about 58.8 PSI (405 kPa) and may be applied to implantable device 10 from all directions for a duration ranging from about 0.5 minute to about 20 minutes.

Figure 6A:
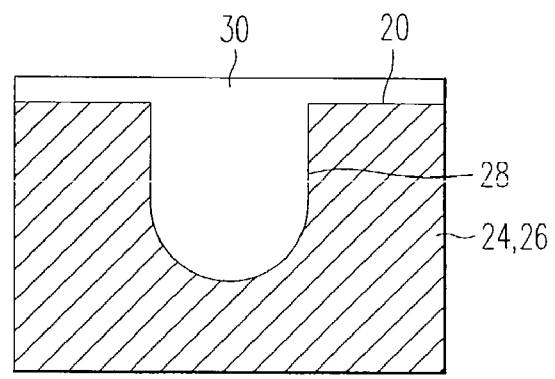
FIGS. 6A, 6B, and 6C illustrate the composition-coated stent of FIG. 3A after an increased pressure has been applied such that the composition is driven into the depot.
Figure 6B:
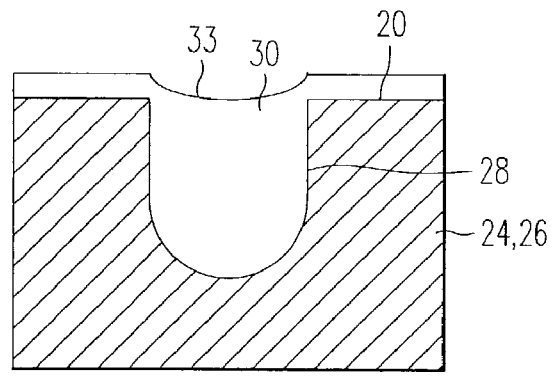
Figure 6C:
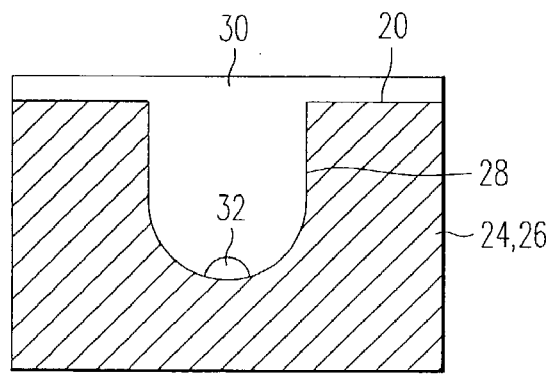

Pressure P drives composition 30 into depots 28 of implantable device 10. As a result, composition 30 may completely displace air pocket 32 within depot 28, such that depot 28 becomes completely filled with composition 30, as depicted in FIGS. 6A and 6B. In other embodiments, composition 30 may partially displace air pocket 32, or alternatively compress air pocket 32 such that air pocket 32 occupies a smaller portion of depot 28 after the pressure treatment than before the pressure treatment, as depicted in FIG. 6C. Composition 30 may not be of uniform thickness along outer surface 20 following the pressure treatment in act 104. For example, as shown in FIG. 6B, a dimple 33 may form in composition 30 above depot 28.

Figure 7A:
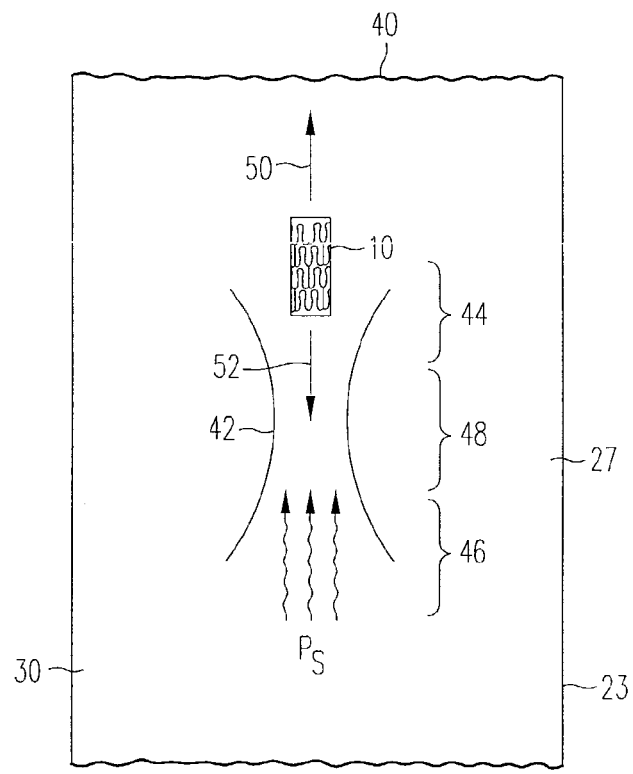
FIG. 7A is a simplified illustration of an embodiment of a coating application chamber for applying an increased non-symmetric pressure applied to the implantable device of FIG. 1A.
Figure 7B:
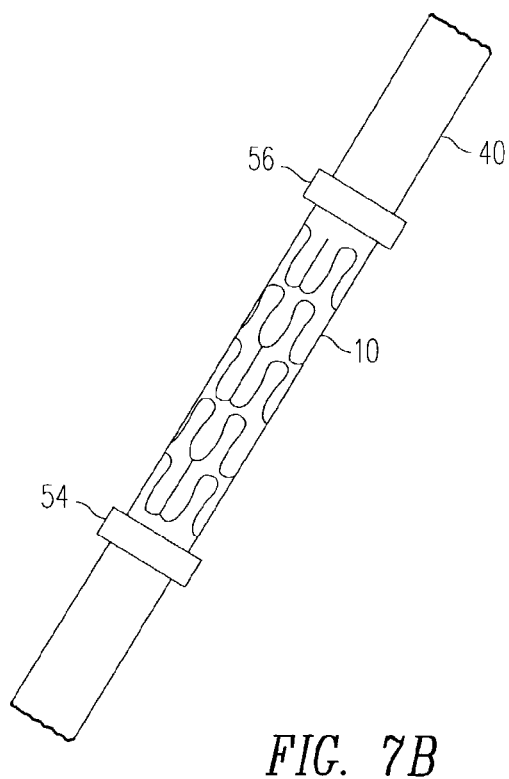
FIG. 7B is a simplified illustration of a mandrel for use with the device of FIG. 7A.

In another embodiment, with reference to FIGS. 4, 7A, and 7B, a non-symmetric pressure $P_S$ can be applied to implantable device 10 in act 104. In this embodiment, implantable device 10 can be inserted into a funnel device 42 disposed in airtight chamber 23 in a bath 27 of composition 30. In one embodiment, as shown in FIG. 7A, funnel device 42 can include a converging section 44, a diverging section 46 and a throat section 48. Implantable device 10 is moved through converging section 44 and into throat section 48. As implantable*device 10 enters throat section 48 an amount of composition 30 is pulled/pushed into throat section 48, as well. The amount of composition 30 entering throat section 48 becomes compressed, which causes a change in pressure in throat section 48. The pressure moves as a wave of pressure $P_S$ along a longitudinal axis of implantable device 10. Optionally, implantable device 10 can be moved back and forth through funnel device 42, as indicated by arrows 50 and 52. In this optional embodiment, pressure wave $P_S$ is set up to move over implantable device 10 as implantable device 10 is moved in either direction. Decreasing the separation between the outside diameter of implantable device 10 and the inner diameter of throat section 48 causes the pressure in throat section 48 to increase.

FIG. 7B is a simplified illustration of an embodiment of a mandrel 40, which can be used to support implantable device 10 as the device is made to move through funnel device 42. In this embodiment, mandrel 40 can be a solid cylindrical member with an outside diameter approximately equal to the inside diameter of implantable device 10, such that implantable device 10 is held on to mandrel 40 with an interference fit. Optionally, anchors 54 and 56, such as a screw-on collars as are known in the art, can be used with mandrel 40 to hold implantable device 10 in position. In one example, the thickness of anchors 54 and 56 are approximately equal to the thickness of implantable device 10, with an outside diameter no greater than the diameter of throat section 48.

Figure 8A:
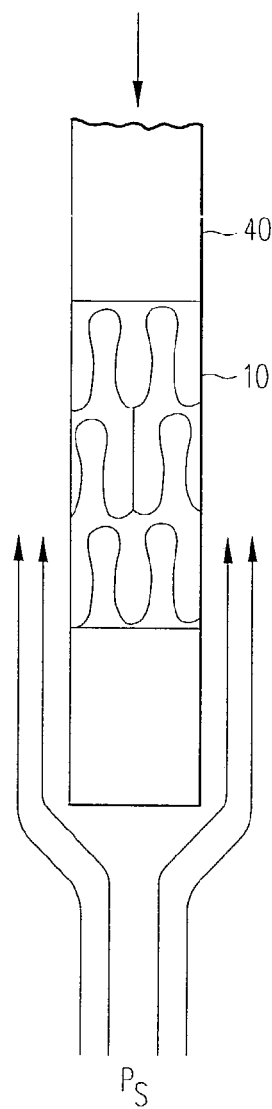
FIG. 8A is a simplified illustration of a non-symmetric pressure being applied to the implantable device mounted on the mandrel of FIG. 7B.
Figure 8B:
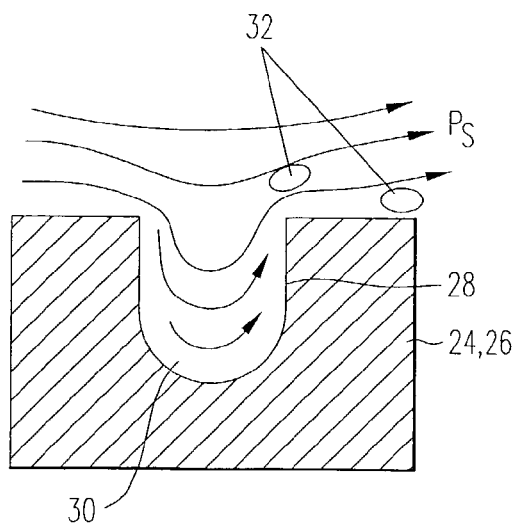
FIG. 8B is a simplified illustration of the composition-coated implantable device having a non-symmetric increased pressure applied such that the composition is driven into the depot.

As best understood with reference to FIG. 8A, mandrel 40 blocks backward flow out from the center of funnel device 42 to increase the pressure build-up around the outside diameter of implantable device 10 to create a pressure gradient over depots 28. As illustrated in FIG. 8B, the longitudinally applied pressure wave $P_S$ forces composition 30 into depot 28. The force of the pressure wave $P_S$ breaks through surface tension or molecular cohesion forces within composition 30 to allow gas bubble 32, or a plurality of gas bubbles 32, to escape or be removed out from depot 28. In an alternative embodiment, mandrel 40 can be used to spin, vibrate, and/or otherwise agitate implantable device 10 by spinning, vibrating, and/or otherwise agitating mandrel 40 within bath 27 of composition 30.

Figure 9:
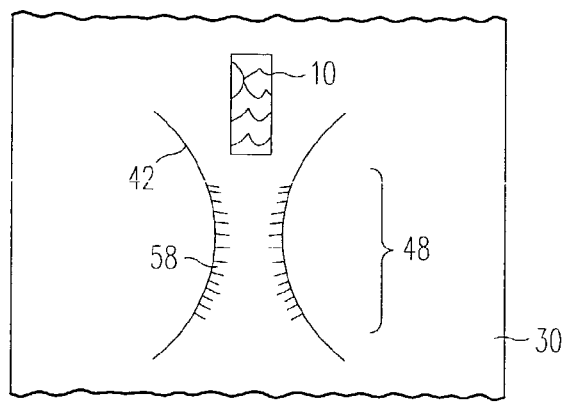
FIG. 9 is a simplified illustration of an alternative embodiment of the coating application chamber of FIG. 7A.

FIG. 9 illustrates another embodiment of throat section 48, which includes bristles 58 disposed along the inner wall of throat section 48. Bristles 58 can rub or scrub composition 30 into depots 28. Bristles 58 can aid in breaking through surface tension or molecular cohesion forces in composition 30 to allow the release of gas bubbles from depots 28. Bristles 58 can be sized approximately the same as the depth of depots 28.

Figure 10A:
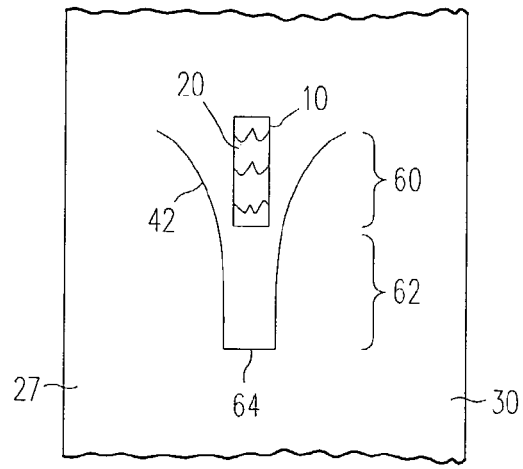
FIGS. 10A and 10B are simplified illustrations of yet another embodiment of the coating application chamber of FIG. 7A.
Figure 10B:
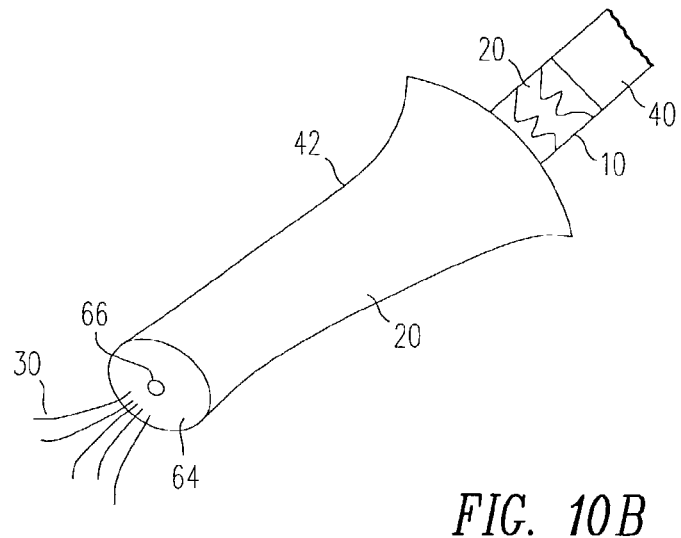

FIG. 10A is a simplified illustration of another embodiment of funnel device 42. In this embodiment, funnel device 42 includes a converging section 60 and a throat section 62. End 64 of funnel device 42, opposite converging section 60, can be either open or closed. In the closed configuration, a greater pressure build-up around the outer surface 20 of implantable device 10 can be created. Alternatively, as shown in FIG. 10B, end 64 can include a small vent hole 66 that allows some amount of composition 30 to pass through, such that the pressure forces in funnel device 42 do not become prohibitive to inserting implantable device 10.

In an alternative embodiment, a method of coating implantable device 10 (FIG. 2A) having depots 28 (FIG. 2B) includes applying composition 30, including a polymer, a solvent and a therapeutic substance to a first surface of the implantable device. The increased pressure forces pockets of gas out of the depots. The solvent is removed from composition 30 on implantable device 10 to form a coating. Optionally, the composition or the coating may be removed from portions of the implantable device outside of depots 28 yielding an implantable device having a coating solely within the depots. In addition, a polymeric topcoat containing a solvent may be applied on at least a portion of the coating. An example of this alternative method is disclosed in U.S. patent application Ser. No. 09/690,907, filed Oct. 17, 2000, which is herein incorporated by reference for all purposes.

What follows is an exemplary embodiment of the present invention, which is presented with no intent to limit the invention thereby. In this example, implantable device 10 has an outside diameter of about 0.070 inches and an inside diameter of about 0.060 inches. The length of implantable device 10 can be any length, for example a length between about 8 mm and 100 mm. Implantable device 10 is mounted on mandrel 40. In this example, the outside diameter of mandrel 40 is about 0.063, with a length that is long enough to accommodate implantable device 10 and anchors 54 and 56. Anchors 54 and 56 have an outside diameter of about 0.069. In this example, throat section 48 is designed to correspond to the outside diameter of implantable device, since decreasing the separation between the outside diameter of implantable device 10 and the diameter of throat section 48 causes the pressure in throat section 48 to increase. Accordingly, funnel device 42 includes throat section 48 having a diameter of between about 0.072 inches and about 0.090 inches and a length of about 5 mm when the second end of the funnel device 42 is closed or semi-closed. In a funnel device having two open ends, throat section 48 may have a length of between about 3 mm and about 30 mm. The converging/diverging sections of funnel device 42 can have a length of about 10 mm or greater, which enter throat section 48 at an angle between about 1° and about 30°.

While particular embodiments and applications of the present invention have been shown and described, those of ordinary skill in the art will appreciate that changes and modifications can be made without departing from this invention in its broader aspects. This invention may be provided in other specific forms and embodiments without departing from the essential characteristics as described herein. For example, some combination of each embodiment may be made to create additional embodiments. The embodiments described above are to be considered in all aspects as illustrative only and not restrictive in any manner. The following claims rather than the foregoing description indicate the scope of the invention. Therefore, the appended claims are to encompass within their scope all such changes and modifications as fall within the scope of this invention.

What is claimed is:

1. An apparatus for loading depots of an implantable medical device with a substance, comprising:
    a mandrel capable of supporting an implantable medical device having at least one depot in the surface of the device; and
    a funnel adapted to be disposed in a bath of a substance, wherein at least a portion of the funnel includes bristles; and
    wherein the mandrel is moveable within the funnel to create a pressure gradient over the implantable medical device which reduces a surface tension of the substance causing the substance to be loaded into the depot.

2. The apparatus of claim 1, wherein the funnel has a first open end and a throat, the throat being lined with the bristles for reducing the surface tension.

3. The apparatus of claim 1, wherein the funnel has a first open end, a second open end and a throat in between the ends.

4. The apparatus of claim 1, wherein the implantable device is a stent and wherein the substance includes a therapeutic substance.

5. The apparatus of claim 1, wherein the mandrel is agitatable, spinnable, or vibratable in the funnel.

6. The apparatus of claim 1, wherein the funnel includes a first diameter, a second diameter and a third diameter, and wherein the third diameter is smaller than the first and second diameters and is positioned between the first and second diameters.

7. The apparatus of claim 1, wherein the funnel includes an open end for receiving the implantable device and a sealed end opposing the open end to prevent passage of the substance through the sealed end.

8. The apparatus of claim 1, wherein the funnel includes a first open end for receiving the implantable device and a second end having a barrier to prevent passage of a portion of the substance through the second end, the barrier optionally including an aperture for allowing a portion of the substance to discharge from the aperture.

9. An apparatus for loading a composition into pores of an implantable medical device, comprising:
    a chamber containing a composition;
    a mandrel supporting an implantable medical device in the chamber; and
    a funnel disposed in the chamber for receiving the mandrel having the implantable device supported thereon, wherein at least a portion of the funnel includes bristles.

10. The apparatus of claim 9, wherein the funnel has a first diameter and a second diameter smaller than the first diameter.

11. The apparatus of claim 10, wherein the implantable device is a stent and the outer diameter of the stent as inserted in the funnel is slightly smaller than the second diameter.

12. The apparatus of claim 10, wherein the funnel additionally includes a third diameter larger than the second diameter and wherein the second diameter is positioned between the first and third diameters.

13. The apparatus of claim 9, wherein the funnel is capable of causing a pressure to be applied to the composition to load the composition into the pores when the implantable device is moved within the funnel.

14. The apparatus of claim 9, wherein the composition includes a polymer dissolved in a solvent and a therapeutic substance added thereto.

15. The apparatus of claim 9, wherein the funnel includes an open end for receiving the implantable device and a sealed end opposing the open end to prevent passage of the composition through the sealed end.

16. The apparatus of claim 9, wherein the funnel includes a first open end for receiving the implantable device and a second end having a barrier to prevent passage of a portion of the composition through the second end, the barrier optionally including an aperture for allowing a portion of the composition to discharge from the aperture.

17. The apparatus of claim 9, wherein the implantable device is a stent.

18. The apparatus of claim 9, wherein the chamber is airtight.

\* \* \* \* \*